United States Patent
Teleki et al.

(10) Patent No.: US 9,675,557 B2
(45) Date of Patent: *Jun. 13, 2017

(54) PROCESS FOR THE PRODUCTION OF DISCRETE SOLID EXTRUDED PARTICLES

(71) Applicant: DSM IP ASSETS B.V., Heerlen (NL)

(72) Inventors: Alexandra Teleki, Basel (CH); Elger Funda, Basel (CH); Leonardus Gerardus Bernardus Bremer, Basel (CH); Pierre Elemans, Basel (CH); Adriaan Willem Meesen, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/647,385

(22) PCT Filed: Nov. 27, 2013

(86) PCT No.: PCT/EP2013/074879
§ 371 (c)(1),
(2) Date: May 26, 2015

(87) PCT Pub. No.: WO2014/083065
PCT Pub. Date: Jun. 5, 2014

(65) Prior Publication Data
US 2015/0297522 A1    Oct. 22, 2015

(30) Foreign Application Priority Data
Nov. 27, 2012    (EP) .................................... 12194395

(51) Int. Cl.
A61K 9/16    (2006.01)
A61K 8/73    (2006.01)
(Continued)

(52) U.S. Cl.
CPC .......... A61K 9/1682 (2013.01); A23K 20/174 (2016.05); A23L 27/72 (2016.08);
(Continued)

(58) Field of Classification Search
CPC .......... A23V 2002/00; A23V 2200/224; A23V 2250/51084; A23V 2250/702;
(Continued)

(56) References Cited

U.S. PATENT DOCUMENTS 2,299,929 A * 10/1942 Raynolds, Jr. ........... A61K 9/16
264/13
2007/0098853 A1    5/2007 Van Lengerich
(Continued)

FOREIGN PATENT DOCUMENTS

EP    1 116 515    7/2001
EP    2 692 331    2/2014
(Continued)

OTHER PUBLICATIONS

International Search Report for PCT/EP2013/074879 mailed Apr. 3, 2014, four pages.

*Primary Examiner* — Aradhana Sasan
(74) *Attorney, Agent, or Firm* — Nixon & Vanderhye P.C.

(57) ABSTRACT

The present invention relates to a process for the production of discrete solid extruded particles comprising emulsion droplets, to such particles as well as to the use of such particles in food, feed, pharmaceutical and personal care applications.

26 Claims, 1 Drawing Sheet

Schematic of the process for production of extruded, solid particles comprising emulsified lipophilic active.

(51) Int. Cl.
*A61K 8/34* (2006.01)
*A61K 8/02* (2006.01)
*B29B 9/06* (2006.01)
*B29B 9/12* (2006.01)
*B29B 9/16* (2006.01)
*A23K 20/174* (2016.01)
*A23P 10/30* (2016.01)
*A23P 30/20* (2016.01)
*A23L 27/00* (2016.01)
*A23L 33/155* (2016.01)
*B29K 105/00* (2006.01)
*B29L 31/00* (2006.01)

(52) U.S. Cl.
CPC ............. *A23L 27/80* (2016.08); *A23L 33/155* (2016.08); *A23P 10/30* (2016.08); *A23P 30/20* (2016.08); *A61K 8/0241* (2013.01); *A61K 8/342* (2013.01); *A61K 8/731* (2013.01); *A61K 8/732* (2013.01); *A61K 9/1652* (2013.01); *B29B 9/06* (2013.01); *B29B 9/12* (2013.01); *A23V 2002/00* (2013.01); *A61K 2800/10* (2013.01); *A61K 2800/412* (2013.01); *B29B 2009/166* (2013.01); *B29K 2105/0064* (2013.01); *B29L 2031/718* (2013.01); *B29L 2031/753* (2013.01)

(58) Field of Classification Search
CPC ........ A23V 2300/16; A23V 2250/5114; A23V 2250/5118; A23K 1/1603; A23L 1/0029; A23L 1/0076; A23L 1/22016; A23L 1/22058; A23L 1/303; A61K 2800/412; A61K 8/0241; A61K 8/342; A61K 8/731; A61K 8/732; A61K 9/1652; A61K 9/1682; B29B 2009/166; B29B 9/06; B29B 9/12; B29L 2031/718; B29L 2031/753

See application file for complete search history.

(56) References Cited

U.S. PATENT DOCUMENTS

| 2008/0206434 | A1 | 8/2008 | Erdmann et al. | |
|---|---|---|---|---|
| 2014/0228429 | A1* | 8/2014 | Funda | A23L 1/0076 514/458 |
| 2015/0056345 | A1* | 2/2015 | Elemans | A23L 1/2753 426/250 |
| 2015/0320683 | A1* | 11/2015 | Teleki | B01J 2/20 424/401 |

FOREIGN PATENT DOCUMENTS

| WO | WO 03/056938 | 7/2003 |
|---|---|---|
| WO | WO 2012/133246 | 10/2012 |
| WO | WO 2012/163836 | 12/2012 |

\* cited by examiner

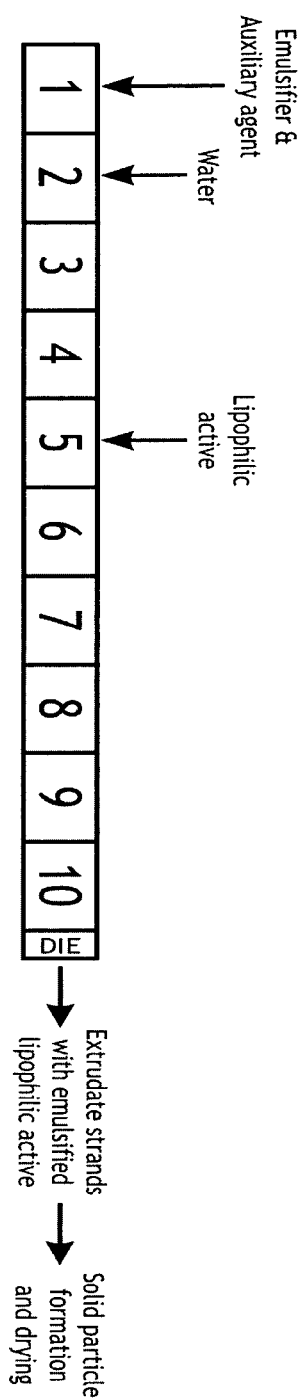
Figure 1. Schematic of the process for production of extruded, solid particles comprising emulsified lipophilic active.

PROCESS FOR THE PRODUCTION OF DISCRETE SOLID EXTRUDED PARTICLES

This application is the U.S. national phase of International Application No. PCT/EP2013/074879 filed 27 Nov. 2013 which designated the U.S. and claims priority to EP Patent Application No. 12194395.5 filed 27 Nov. 2012, the entire contents of each of which are hereby incorporated by reference.

The present invention relates to a process for the production of discrete solid extruded particles comprising emulsion droplets, to such particles as well as to the use of such particles in food, feed, pharmaceutical and personal care applications.

There are many ways to formulate fat soluble compounds. Fat soluble compounds are for example oils and vitamins. The types of formulations are depending i.e. on the use of these formulations in the final application as well as on the kind of material (ingredients) which are used.

One way to formulate fat soluble compounds are dried emulsions. The fat soluble compound is emulsified in an oil-in-water emulsion wherein the aqueous phase contains a matrix material and/or a suitable emulsifier. After drying, the fat soluble compound is embedded in the matrix material.

Known technologies for emulsification are e.g. rotor-stator-systems, high pressure homogenizers or ultrasonic devices. A major disadvantage of these technologies is that a relatively low viscosity (usually below 1 Pas) is required, leading to high amounts of water in the emulsion, which needs to be removed at the end.

Extrusion processes (and extruders) are well known in the field of formulations. They can be used for many different kinds of materials. The technology was first used in the caoutchouc (natural gum) industry. But after some time, the food and feed industry adopted this technology for their purposes as well.

The main advantages of using the extrusion technology are that high viscous solutions can be formulated and less water can be used for the dispersion, which then requires less drying. Furthermore an extrusion process can be run as a continuous process.

It can be found in the prior art that emulsions comprising fat soluble vitamins are extruded. US 2004/0201116 discloses pellets which are obtained by a combination of producing emulsions using devices like high pressure homogenizers with subsequent direct pelleting or extrusion as a second process step.

The goal of the present invention was to find a way to improve (also simplify) the production of extrudates comprising oil-in-water emulsion droplets, which comprise fat soluble compound(s), such as for example oils or vitamins.

These extrudates should then also be formed into a good flowable form which has a low fraction of the oil-in-water emulsion droplets on the particle surface (low surface oil content).

In the context of the present invention the term extrudate is defined as the product form which is coming out of the extruder and which is not yet further processed.

A new way for the production of such discrete solid extruded particles was found. Surprisingly it was found out that when the emulsification is carried out inside the extruder, and then afterward the extrudates are further formed into discrete solid extruded particles, the process as well as the obtained extrudates and discrete solid extruded particles are improved.

When the emulsification is carried out in the extruder (extrusion apparatus), and wherein afterward the extrudates are further formed into discrete solid extruded particles,
(i) very small average dispersion droplets sizes can be obtained, and
(ii) a very narrow and monomodal distribution of the droplet sizes is obtained, and
(iii) such a process can easily be run as a continuous process, and
(iv) no organic solvent is used and
(v) less water can be used and therefore less energy for drying the extrudate is necessary, and
(vi) good flowability of the discrete solid extruded particles, and
(vii) low surface oil content of the discrete solid extruded particles (less than 1%).

Therefore the present invention relates to a process of production of discrete solid extruded particles, wherein an extrudate comprising oil-in-water emulsion droplets is produced in a first step,
and after the extrusion the extrudate is further formed into discrete solid extruded particles.

A preferred embodiment of the present invention relates to a process as described above, wherein the oil-in-water emulsion droplets comprising at least one fat soluble compound and at least one emulsifier and water, and wherein the emulsifying process is carried out in the extruder.

A preferred embodiment of the present invention relates to a process as described above wherein the extrudate is further formed into discrete solid extruded particles by cutting and drying.

A preferred embodiment of the present invention relates to a process as described above wherein the drying can be carried out before cutting, during the cutting or after the cutting, as well as a combination thereof.

A preferred embodiment of the present invention relates to a process as described above wherein the extrudate is further formed into discrete solid extruded particles by a spheronisation process.

As fat soluble compounds any known and useful fat soluble compounds can be used. Fat soluble compounds are compounds soluble in non-polar substances (such as ether, chloroform and oils). Examples of fat soluble compounds are i.e. oils and vitamins.

The oils can be from any origin. They can be natural, modified or synthetic. If the oils are natural they can be plant or animal oils. Suitable oils are i.e. coconut oil, corn oil, cottonseed oil, olive oil, palm oil, peanut oil, rapeseed oil, canola oil, safflower oil, sesame oil, soybean oil, sunflower oil, hazelnut oil, almond oil, cashew oil, macadamia oil, mongongo nut oil, pracaxi oil, pecan oil, pine nut oil, pistachio oil, sacha Inchi (*Plukenetia volubilis*) oil, walnut oil, polyunsaturated fatty acids (such as triglyceride and/or ethyl ester, (for example arachidonic acid, eicosapentaenoic acid, docosahexaenoic acid and γ-linolenic acid and/or ethyl ester) and oily nutraceuticals (such as rosemary extract, oregano extract, hop extract, and other lipophilic plant extracts).

Polyunsaturated fatty acids (PUFAs) are classified according to the position of the double bonds in the carbon chain of the molecule as n-9, n-6 or n-3 PUFAs. Examples of n-6 PUFAs are linoleic acid (C18:2), arachidonic acid (ARA, C20:4), γ-linolenic acid (GLA, C18:13) and dihomo-γ-linolenic acid (DGLA, C20:3). Examples of n-3 PUFAs are α-linolenic acid (C18:13), eicosapentaenoic acid (EPA, C20:5), and docosahexaenoic acid (DHA, C22:6).

Fat soluble vitamins such as vitamin A or its esters (for example vitamin A acetate and vitamin A palmitate), vitamin E or its esters (for example vitamin E acetate), vitamin K (phytomenadione) and vitamin D3 (cholecalciferol) are contemplated in the present invention. Such vitamins are readily available from commercial sources. Also, they may be prepared by conventional methods by a skilled person. Vitamins may be used in pure form, or in a suitable diluent such as a fat or oil.

Vitamin A and/or retinyl esters, such as e.g. retinyl palmitate and/or retinyl acetate and vitamin E or its esters (for example vitamin E acetate) are especially preferred.

Therefore a preferred embodiment of the present invention relates to a process as described above, wherein the fat soluble compound is at least one oil and/or at least one fat soluble vitamin.

More preferred is a process wherein one or more fat soluble compound is chosen from the group consisting of coconut oil, corn oil, cottonseed oil, olive oil, palm oil, peanut oil, rapeseed oil, canola oil, safflower oil, sesame oil, soybean oil, sunflower oil, hazelnut oil, almond oil, cashew oil, macadamia oil, mongongo nut oil, pracaxi oil, pecan oil, pine nut oil, pistachio oil, sacha Inchi (*Plukenetia volubilis*) oil, walnut oil, PUFAs (such as triglyceride and/or ethyl ester, for example arachidonic acid, eicosapentaenoic acid, docosahexaenoic acid and γ-linolenic acid and/or ethyl ester, was well as linoleic acid, arachidonic acid, γ-linolenic acid, dihomo-γ-linolenic acid, α-linolenic acid, eicosapentaenoic acid and docosahexaenoic acid), oily nutraceuticals (such as rosemary extract, oregano extract, hop extract, and other lipophilic plant extracts), vitamin A or its esters (for example vitamin A acetate and vitamin A palmitate), vitamin E or its esters (for example vitamin E acetate), vitamin K (phytomenadione) and vitamin D3 (cholecalciferol).

In an especially preferred process one or more fat soluble compound is chosen from the group consisting of corn oil, vitamin A or its esters (for example vitamin A acetate and vitamin A palmitate), vitamin E or its esters (for example vitamin E acetate) and PUFAs (especially linoleic acid, arachidonic acid, γ-linolenic acid, dihomo-γ-linolenic acid, α-linolenic acid, eicosapentaenoic acid and docosahexaenoic acid).

At least one emulsifier is used in the process according to the present invention. Any commonly known and used emulsifier can be used. The emulsifier can be chosen depending on the final use of the discrete solid extruded particles afterwards. That means if the discrete solid extruded particles obtained by the process according to the present invention are used in food or feed product, the emulsifier must be food or feed grade.

And in case they are used in pharmaceutical application the emulsifier must be pharma grade.

Suitable emulsifiers are i.e. modified (food) starches, pectin, alginate, carrageenan, furcellaran, chitosan, maltodextrin, dextrin derivatives, celluloses and cellulose derivatives (e.g. cellulose acetate, methyl cellulose, hydroxypropyl methyl cellulose), lignosulfonate, polysaccharide gums (such as gum acacia, gum arabic, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof).

The starches can be modified physically and chemically. Pregelatinized starches are examples of physically modified starches. Acidic modified, oxidized, cross-linked, starch esters, starch ethers and cationic starches are examples of chemically modified starches.

A preferred embodiment of the present invention relates to a process, wherein at least one emulsifier is chosen from the group consisting of modified (food) starches, pectin, alginate, carrageenan, furcellaran, chitosan, maltodextrin, dextrin derivatives, celluloses and cellulose derivatives (e.g. cellulose acetate, methyl cellulose, hydroxypropyl methyl cellulose), lignosulfonate, polysaccharide gums (such as gum acacia, gum arabic, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof).

A more preferred embodiment of the present invention relates to a process, wherein at least one emulsifier is a (modified) food starch. This means that the process can be carried out with one emulsifier only (which is a (modified) food starch) or with a mixture of emulsifiers wherein either all of them are (modified) food starches or at least one in the mixture.

Water is also used in the process according to the present invention. But as mentioned before, it is possible to run the process with less water when compared to the usually used processes.

No organic solvent is used in the process according to the present invention.

It is also possible to add further ingredients (auxiliary agents) during the process of formulation (extrusion).

Such auxiliary agents can be useful for the extrusion process
and/or for the extrudate,
and/or for the discrete solid particles,
and/or for the product (or application), wherein the discrete solid extruded particles are used afterwards.

Such auxiliary agents are for example
antioxidants (such as ascorbic acid or salts thereof, tocopherol (synthetic or natural)), butylated hydroxytoluene (BHT), ascorbyl palmitate, butylated hydroxyanisole (BHA), propyl gallate, tert. butyl hydroxyquinoline, ethoxyquin and/or ascorbic acid esters of a fatty acid);
plasticisers (such as fructose, glucose, glycerol, mannitol, invert sugar syrup, sorbitol, sucrose, xylitol, propylene glycol, ester of citric acid, lactitol, erythritol and maltitol);
stabilisers;
humectants (such as glycerine, sorbitol, polyethylene glycol);
protective colloids (such as gellan gum, xanthan gum);
dyes;
fragrances;
fillers and
buffers.

These auxiliary agents are added optionally. When added then the amount of the auxiliary agents goes from 1 to 85 weight-% (wt.-%), based on the total weight of the extrudate.

All the preferences listed above for the fat soluble compounds, the emulsifiers and the auxiliary agents also apply to the composition of the extrudates as well as to the discrete solid extruded particles.

The amounts given for the emulsion are equivalent to the amount of the extrudate (and therefore the amounts which are fed into the extruder, which forms therein the emulsion), because there is almost no loss of material (especially water) during the extrusion process.

In a preferred process according to the present invention 5 wt.-% to 75 wt.-%, preferably 8 wt.-% to 70 wt.-%, based on the total weight of the emulsion, of at least one fat soluble compound are used.

In a preferred process according to the present invention 5 wt.-% to 80 wt.-%, more preferably 8 wt.-% to 80 wt.-%, even more preferably 10 wt.-% to 80 wt.-%, based on the total weight of the emulsion, of at least one emulsifier are used.

In a preferred process according to the present invention 1 wt.-% to 90 wt.-%, more preferably 1 wt.-% to 80 wt.-%, based on the total weight of the emulsion, of water are used.

In a preferred process according to the present invention 1 wt.-% to 80 wt.-%, based on the total weight of the emulsion, of at least one auxiliary agent are used.

Therefore a preferred embodiment of the present invention relates to a process of production of discrete solid extruded particles, wherein an extrudate comprising oil-in-water emulsion droplets is produced in a first step,
wherein the emulsion comprises
8 wt.-% to 70 wt.-%, based on the total weight of the emulsion, of at least one fat soluble compound, and
8 wt.-% to 80 wt.-%, preferably 10 wt.-% to 80 wt.-%, based on the total weight of the emulsion, of at least one emulsifier, and
1 wt.-% to 80 wt.-%, based on the total weight of the emulsion, of water and
1 wt.-% to 80 wt.-%, based on the total weight of the emulsion, of at least one auxiliary agent, and
wherein after the extrusion the extrudate is further formed into discrete solid extruded particles.

Therefore a preferred embodiment of the present invention relates to a process of production of discrete solid extruded particles, wherein an extrudate comprising oil-in-water emulsion droplets is produced in a first step,
wherein the emulsion comprises
8 wt.-% to 70 wt.-%, based on the total weight of the emulsion, of at least one fat soluble compound chosen from the group consisting of coconut oil, corn oil, cottonseed oil, olive oil, palm oil, peanut oil, rapeseed oil, canola oil, safflower oil, sesame oil, soybean oil, sunflower oil, hazelnut oil, almond oil, cashew oil, macadamia oil, mongongo nut oil, pracaxi oil, pecan oil, pine nut oil, pistachio oil, sacha Inchi (*Plukenetia volubilis*) oil, walnut oil, PUFAs (such as triglyceride and/or ethyl ester, (for example arachidonic acid, eicosapentaenoic acid, docosahexaenoic acid and γ-linolenic acid and/or ethyl ester; as well as linoleic acid, arachidonic acid, γ-linolenic acid, dihomo-γ-linolenic acid, α-linolenic acid, eicosapentaenoic acid and docosahexaenoic acid), oily nutraceuticals (such as rosemary extract, oregano extract, hop extract, and other lipophilic plant extracts), vitamin A or its esters (for example vitamin A acetate and vitamin A palmitate), vitamin E or its esters (for example vitamin E acetate), vitamin K (phytomenadione) and vitamin D3 (cholecalciferol), and
8 wt.-% to 80 wt.-%, preferably 10 wt.-% to 80 wt.-%, based on the total weight of the emulsion, of at least one emulsifier chosen from the group consisting of modified (food) starches, pectin, alginate, carrageenan, furcellaran, chitosan, maltodextrin, dextrin derivatives, celluloses and cellulose derivatives (e.g. cellulose acetate, methyl cellulose, hydroxypropyl methyl cellulose), lignosulfonate, polysaccharide gums (such as gum acacia, gum arabic, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof), and
1 to 80 wt.-%, based on the total weight of the emulsion, of water and
1 to 80 wt.-%, based on the total weight of the emulsion, of at least one auxiliary agent chosen from the group consisting of antioxidants (such as ascorbic acid or salts thereof, tocopherol (synthetic or natural); butylated hydroxytoluene (BHT); butylated hydroxyanisole (BHA); ascorbyl palmitate; propyl gallate; tert. butyl hydroxyquinoline, ethoxyquin, and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers; humectants (such as glycerine, sorbitol, polyethylene glycol); protective colloids (preferably gellan gum and xanthan gum); dyes; fragrances; fillers and buffers, and
wherein after the extrusion the extrudate is further formed into discrete solid extruded particles.

Therefore a more preferred embodiment of the present invention relates to a process of production of discrete solid extruded particles, wherein an extrudate comprises oil-in-water emulsion droplets is produced in a first step,
wherein the emulsion comprises
8 wt.-% to 70 wt.-%, based on the total weight of the emulsion, of at least one fat soluble compound chosen from the group consisting of corn oil, vitamin A or its esters (for example vitamin A acetate and vitamin A palmitate), vitamin E or its esters (for example vitamin E acetate) and polyunsaturated fatty acids (preferably linoleic acid, arachidonic acid, γ-linolenic acid, dihomo-γ-linolenic acid, α-linolenic acid, eicosapentaenoic acid and docosahexaenoic acid, and
10 wt.-% to 80 wt.-%, based on the total weight of the emulsion, of at least one emulsifier which is a (modified) food starch, and
1 to 80 wt.-%, based on the total weight of the emulsion, of water and
1 to 80 wt.-%, based on the total weight of the emulsion, of at least one auxiliary agent chosen from the group consisting of antioxidants (such as ascorbic acid or salts thereof, tocopherol (synthetic or natural); butylated hydroxytoluene (BHT); butylated hydroxyanisole (BHA); ascorbyl palmitate; propyl gallate; tert. butyl hydroxyquinoline, ethoxyquin, and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers; humectants (such as glycerine, sorbitol, polyethylene glycol); protective colloids (preferably gellan gum and xanthan gum); dyes; fragrances; fillers and buffers, and wherein after the extrusion the extrudate is further formed into discrete solid extruded particles.

As stated above the extrudate (which comes out of the extruder) has the same composition as the emulsion.

One of the advantages of the present invention is that the size distribution of the average droplet sizes of the oil-in-water emulsion inside the extrudate (and in the discrete solid extruded particles) is narrow and monomodal. This means that the fat soluble compound is nearly homogenously distributed inside the extrudate (and in the discrete solid extruded particles), which allows afterwards very precise dosages. Furthermore, the process according to the present invention allows producing very small sized droplets of the oil-in-water emulsion inside the extrudate (and in the discrete solid extruded particles). The average droplet size can be as small as 50 nm. Usually the droplets are smaller than 1 µm.

Preferably the average droplet size ($d_{3,2}$) of the oil-in-water emulsion inside the extrudate (and in the discrete solid extruded particles) is between 50 nm and 300 nm. The droplet sizes are measured by using commonly known and standardized methods. Suitable methods are light scattering or laser diffraction.

More preferably the average droplet size ($d_{3,2}$) of the oil-in-water emulsion inside the extrudate (and in the discrete solid extruded particles) is between 100 nm and 200 nm.

The extrusion process is characterised in that the emulsification is carried out inside the extruder. Usually the three main ingredients (fat soluble compound and emulsifier and water) are added at different inlets of the extruder process. These inlets are arranged separated from each other. When (optionally) auxiliary agents are added, they can be added together with one or more of the main ingredients or they can also be added in a separate step.

Usually the emulsifier is added first, then the water and then the fat soluble compound is added. It is also possible that one ingredient is added through more than one inlet of the extruder at different locations. Therefore a further embodiment of the present invention relates to a process, wherein the emulsifier (or a mixture of emulsifiers) is added first, then the water and then afterwards the fat soluble compound (or a mixture of fat soluble compounds).

A preferred embodiment of the present invention relates to a process wherein the fat soluble compound is vitamin A (or a derivative). In this case vitamin A is either added
(i) as a liquid (molten) into the extruder, or
(ii) as a solid powder (optionally premixed with at least one modified (food) starch) and wherein the powder can be added to the process at the start of the extruder or at any stage)

The temperature inside the extruder is usually between 20 and 220° C. Preferably the temperature of extrudate exiting the extruder is <100° C., more preferably the temperature inside the extruder is between 20 and 100° C. The total residence time for the ingredients in the extruder is usually between 1 and 400 s.

The amount of shear of the extrusion process according to the present invention is usually 200 to 80000 units.

Furthermore, it is also possible to pump inert gas through the extruder. The inert gas is usually pumped in at the entrance of the extruder. But it could also be pumped in at any stage of the extrusion process (also through several inlets at different locations). Inert gas can be helpful to protect sensible ingredients.

The extruder comprises usually one or more screw shafts on which various conveying or kneading type screw elements are mounted.

The material is transported by these elements through the extruder (optionally under pressure and elevated temperature). At the end (exit) of the extruder there can be a die through which the extruded material is pressed. Afterwards the extruded material is dried and cut (or also vice versa). The extruder can have several inlets through which the material can be added.

In the case of the present invention there are several inlets to add the emulsifier(s), the fat soluble compound(s), water and optionally the auxiliary agents.

An essential feature of the present invention is that the extrudate is (after the extrusion process) further formed into discrete solid extruded particles.

This forming step can be carried out by using various processes.

It is suitable to carry out this forming step by cutting and drying the extrudate. The drying can be carried out before cutting, during the cutting or after the cutting, as well as any other combination thereof.

The cutting can be carried out by any known device used in the extruder technology. The cutting conditions are related to the desired size of the discrete solid extruded particles.

The drying can be carried out by any known device. The drying conditions are related to the desired size and desired final water content of the discrete solid extruded particles.

It is also suitable to carry out this forming step by a spheronisation process. The spheronisation process ("spheronisation) is a known process. During spheronisation cylindrical extrudate strands are converted into spherical, solid particles. In this process, the extrudate strands are broken down into segments and then rounded until they have the desired shape. Finally they are discharged from the spheroniser and transferred to an optional drying step to obtain the final water content in the pellets.

The present invention also relates to discrete solid extruded particles obtainable by a process (as described above), wherein the discrete solid extruded particles comprise emulsion droplets, wherein these emulsion droplets comprise at least one fat soluble compound and at least one emulsifier and water, characterised in that after the extrusion the extrudate is further formed into the discrete solid extruded particles.

Preferably, the present invention also relates to discrete solid extruded particles obtainable by a process (as described above), wherein the discrete solid extruded particles comprise emulsion droplets, wherein these emulsion droplets comprise at least one fat soluble compound and at least one emulsifier and water, characterised in that after the extrusion the extrudate is further formed into the discrete solid extruded particles, and wherein the emulsifying process is carried out in the extruder. All the preferences as described above also apply for such discrete solid extruded particles obtainable by the inventive process.

A further embodiment of the present invention relates to new discrete solid extruded particles. These inventive discrete solid extruded particles comprise oil-in-water emulsion droplets which have a very small average droplet size, and wherein the distribution of the droplet sizes is narrow and (almost) monomodal.

Furthermore these discrete solid extruded particles do have a low surface oil content.

The surface oil content of the discrete solid extruded particles according to the present invention is lower than 1% (defined by the amount of oil present on the surface, over the total oil content of the discrete solid extruded particle), more preferred lower than 0.5%, most preferred lower than 0.1%.

The particle sizes of the discrete solid extruded particles are lower than 1000 µm. preferably lower than 700 µm. Usually between 50-700 µm.

It is also possible to produce discrete solid extruded particles having a particle size between 50-500 µm or having a particle size between 100-400 µm.

The particle size distribution of the discrete solid extruded particles is quite narrow. The shape of the discrete solid extruded particles is preferably spherical.

The particle size and shape are determined by using well known methods, such as optical microscopy, (scanning) electron microscopy or laser diffraction (only for size). The particle size in the context of the present invention is defined as the longest dimension of a particle (such i.e. the diameter in case of spherical particle or in case of non-spherical particles the diameter of an equivalent sphere).

Therefore a further embodiment of the present invention relates to discrete solid extruded particles comprising oil-in-water emulsion droplets, wherein these emulsion droplets comprise
at least one fat soluble compound and
at least one emulsifier, and
water, and optionally
at least one auxiliary agent,
characterised in that the average particle size of the oil-in-water emulsion droplets inside the discrete solid extruded particles are less than 300 nm (preferably the average particle size of the oil-in-water emulsion droplets is between 100 nm and 200 nm), characterised that the discrete solid extruded particles comprise less than 10 wt-%, based on the total weight of the discrete solid extruded particles, of water (preferably less than 6 wt-%).

The average particle size of the oil-in-water emulsion droplets are measured by laser diffraction, e.g. with a Malvern Mastersizer 2000 and Hydro 2000 S sample dispersion unit. The average particle size of the oil-in-water emulsion droplets can also be determined by dynamic light scattering, e.g. with a Malvern Zetasizer Nano.

Preferred discrete solid extruded particles according to the present invention comprise:
5 wt.-% to 75 wt.-%, based on the total weight of the discrete solid extruded particles, of at least one fat soluble compound, and
5 wt.-% to 80 wt.-%, based on the total weight of the discrete solid extruded particles, of at least one emulsifier, and
less than 10 wt.-%, based on the total weight of the discrete solid extruded particles, of water and optionally
1 wt.-% to 85 wt.-%, based on the total weight of the discrete solid extruded particles, of at least one auxiliary agent,
characterised in that the average particle size of the oil-in-water emulsion droplets inside the discrete solid extruded particles are less than 300 nm (preferably the average particle size of the emulsion droplets is between 100 nm and 200 nm).

The particle sizes of these discrete solid extruded particles are lower than 1000 µm. preferably lower than 700 µm. Usually between 50-700 µm.

More preferred are discrete solid extruded particles comprising
8 wt.-% to 70 wt.-%, based on the total weight of the discrete solid extruded particles, of at least one fat soluble compound wherein the fat soluble compound is chosen from the group consisting of coconut oil, corn oil, cottonseed oil, olive oil, palm oil, peanut oil, rapeseed oil, canola oil, safflower oil, sesame oil, soybean oil, sunflower oil, hazelnut oil, almond oil, cashew oil, macadamia oil, mongongo nut oil, pracaxi oil, pecan oil, pine nut oil, pistachio oil, sacha Inchi (*Plukenetia volubilis*) oil, walnut oil, PUFAs (such as triglyceride and/or ethyl ester; for example linoleic acid, arachidonic acid, γ-linolenic acid, dihomo-γ-linolenic acid, α-linolenic acid, eicosapentaenoic acid and docosahexaenoic acid), oily nutraceuticals (such as rosemary extract, oregano extract, hop extract, and other lipophilic plant extracts), vitamin A or its esters (for example vitamin A acetate and vitamin A palmitate), vitamin E or its esters (for example vitamin E acetate), vitamin K (phytomenadione) and vitamin D3 (cholecalciferol), and 8 wt.-% to 80 wt.-%, based on the total weight of the discrete solid extruded particles, of at least one emulsifier, wherein the emulsifier is chosen from the group consisting of modified (food) starches, pectin, alginate, carrageenan, furcellaran, chitosan, maltodextrin, dextrin derivatives, celluloses and cellulose derivatives (e.g. cellulose acetate, methyl cellulose, hydroxypropyl methyl cellulose), lignosulfonate, polysaccharide gums (such as gum acacia, gum arabic, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof), and less than 6 wt.-%, based on the total weight of the discrete solid extruded particles, of water, and 1 wt.-% to 80 wt.-%, based on the total weight of the discrete solid extruded particles, of at least one auxiliary agent, wherein the auxiliary agent is chosen from the group consisting of antioxidants (such as ascorbic acid or salts thereof, tocopherol (synthetic or natural)), butylated hydroxytoluene (BHT), ascorbyl palmitate, butylated hydroxyanisole (BHA), propyl gallate, tert. butyl hydroxyquinoline, ethoxyquin and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers; humectants (such as glycerine, sorbitol, polyethylene glycol); protective colloids (such as gellan gum and xanthan gum); dyes; fragrances; fillers and buffers, characterised in that the average particle size of the oil-in-water emulsion droplets inside the discrete solid extruded particles is less than 300 nm (preferably the average particle size of the emulsion droplets is between 100 nm and 200 nm) and wherein the particle sizes of the discrete solid extruded particles are lower than 1000 µm (preferably lower than 700 µm, more preferably between 50-700 µm).

Furthermore preferred are discrete solid extruded particles comprising
8 wt.-% to 70 wt.-%, based on the total weight of the discrete solid extruded particles, of at least one fat soluble compound wherein the fat soluble compound is chosen from the group consisting of corn oil, vitamin A or its esters (for example vitamin A acetate and vitamin A palmitate), vitamin E or its esters (for example vitamin E acetate) and polyunsaturated fatty acids (preferably linoleic acid, arachidonic acid, γ-linolenic acid, dihomo-γ-linolenic acid, α-linolenic acid, eicosapentaenoic acid and docosahexaenoic acid), and 8 wt.-% to 80 wt.-%, based on the total weight of the discrete solid extruded particles, of at least one emulsifier, which is a (modified) food starch, and less than 6 wt.-%, based on the total weight of the discrete solid extruded particles, of water, and 1 wt.-% to 80 wt.-%, based on the total weight of the discrete solid extruded particles, of at least one auxiliary agent, wherein the auxiliary agent is chosen from the group consisting of antioxidants (such as ascorbic acid or salts thereof, tocopherol (synthetic or natural)), butylated hydroxytoluene (BHT), ascorbyl palmitate, butylated hydroxyanisole (BHA), propyl gallate, tert. butyl hydroxyquinoline, ethoxyquin and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers; humectants (such as glycerine, sorbitol, polyethylene glycol); protective colloids (such as gellan gum and xanthan gum); dyes; fragrances; fillers and buffers, characterised in that the average particle size of the oil-in-water emulsion droplets inside the discrete solid extruded particles is less than 300 nm (preferably the average particle size of the emulsion droplets is between 100 nm and 200 nm) and wherein the particle sizes of the discrete solid extruded particles are lower than 1000 μm (preferably lower than 700 μm, more preferably between 50-700 μm).

Most preferred are discrete solid extruded particles comprising 8 wt.-% to 35 wt.-%, based on the total weight of the discrete solid extruded particles, of at least one fat soluble compound wherein the fat soluble compound is chosen from the group consisting of corn oil, vitamin A or its esters (for example vitamin A acetate and vitamin A palmitate), vitamin E or its esters (for example vitamin E acetate) and polyunsaturated fatty acids (preferably linoleic acid, arachidonic acid, γ-linolenic acid, dihomo-γ-linolenic acid, α-linolenic acid, eicosapentaenoic acid and docosahexaenoic acid), and 25 wt.-% to 70 wt.-%, based on the total weight of the discrete solid extruded particles, of at least one (modified) food starch, and less than 6 wt.-%, based on the total weight of the discrete solid extruded particles, of water, and 10 wt.-% to 55 wt.-%, based on the total weight of the discrete solid extruded particles, of at least one auxiliary agent, wherein the auxiliary agent is chosen from the group consisting of antioxidants (such as ascorbic acid or salts thereof, tocopherol (synthetic or natural)), butylated hydroxytoluene (BHT), ascorbyl palmitate, butylated hydroxyanisole (BHA), propyl gallate, tert. butyl hydroxyquinoline, ethoxyquin and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers; humectants (such as glycerine, sorbitol, polyethylene glycol); protective colloids (such as gellan gum and xanthan gum); dyes; fragrances; fillers and buffers, characterised in that the average particle size of the oil-in-water emulsion droplets inside the discrete solid extruded particles is less than 300 nm (preferably the average particle size of the emulsion droplets is between 100 nm and 200 nm) and wherein the particle sizes of the discrete solid extruded particles are lower than 1000 μm (preferably lower than 700 μm, more preferably between 50-700 μm).

The discrete solid extruded particles as obtained by the process as described above can be used in many fields of applications. Preferably the discrete solid extruded particles as disclosed and described above are used in food, feed, pharmaceutical and personal care products.

Therefore a further embodiment of the present invention relates to the use of the discrete solid extruded particles as disclosed and described above in food, feed, pharmaceutical and/or personal care products. It is to be mentioned that dietary supplements are part of our definition of food products.

A further embodiment of the present invention relates to food, feed, pharmaceutical or personal care products comprising discrete solid extruded particles as disclosed and described above.

The so obtained products do have good storage stabilities.

DESCRIPTION OF THE FIGURES

FIG. 1: Schematic of the process for production of extruded, solid particles comprising emulsified lipophilic active.

The following Examples serve to illustrate the invention. All percentages and parts (if not otherwise indicated) are related to the weight. The temperature is given (if not otherwise indicated) in degree Celsius.

EXAMPLES

Example 1

The production of discrete solid extruded particles comprising emulsified Vitamin A acetate was conducted according to the schematic process flow shown in FIG. 1. The emulsifiers (modified food starch) as well as the additive (microcrystalline cellulose) were both gravimetrically fed (Brabender Technologie) into the first barrel of a laboratory-scale co-rotating twin screw extruder (Thermo Fisher Scientific, HAAKE Polylab OS with PTW16/40 OS twin screw extruder). The extruder consisted of 10 (electrically heated and water-cooled) barrels and a die head (12×⌀0.5 mm) with a screw diameter of 16 mm and a length to diameter ratio of 40. Demineralized water was injected into the second barrel. The temperature of barrels 2-10 as well as the die head was set to 50° C. Molten Vitamin A acetate at 70° C. (optionally with added antioxidant such as d,l-alpha tocopherol or butylated hydroxytoluene (BHT)) was injected into barrel 5 and mixed with the modified food starch/microcrystalline cellulose in the downstream barrels. A typical extrudate strand composition is shown in Table 1. The extrudate strands containing the emulsified Vitamin A acetate droplets were collected and transferred into a laboratory-scale spheronizer (R250, Gabler). After spheronisation the spherical, solid particles were dried in a laboratory-scale fluid bed drier (Retsch TG 200) for 60 minutes at 50° C. to obtain a final water content of 5 wt %.

A few hundred milligrams of the discrete solid extruded particles were dissolved in water under gentle stirring and the Vitamin A acetate oil droplet size distribution was measured by laser diffraction with a Malvern Mastersizer 2000 and Hydro 2000 S sample dispersion unit. The resulting surface weighted mean oil droplet diameter ($d_{3,2}$) was 484 nm. The surface oil content of the particles (as determined by extraction with cyclohexane and defined as the content found by extraction over the total Vitamin A acetate content of the particle) was very low, 0.04%. The extruded particle size and shape analysis was performed with a Malvern Morphologi G3S microscope and corresponding software. A 1× objective was used for the analysis of at least 6000 particles dispersed manually onto four glass sample holders (plates). Perfectly spherical particles were defined with a HS Circularity 0.91 in the Morphologi G3S software and thereby a fraction of 64% spheres was found. The mean CE diameter of the thus determined particle number distribution was 685 µm.

TABLE 1

Extrudate strand composition as well as discrete solid extruded particle content of Example 1.

| Ingredient | Extrudate strand composition, wt % of total | Solid particle content, wt % of total |
|---|---|---|
| Modified food starch | 22 | 31 |
| Microcrystalline cellulose | 33 | 47 |
| Water | 33 | 5 |
| Vitamin A acetate | 12 | 17 |

Example 2

The production of discrete solid extruded particles comprising emulsified Vitamin A acetate was conducted according to the schematic process flow shown in FIG. 1. The emulsifiers (modified food starch) as well as the filler (dextrin) were both gravimetrically fed (Brabender Technologie) into the first barrel of a laboratory-scale co-rotating twin screw extruder (Thermo Fisher Scientific, HAAKE Polylab OS with PTW16/40 OS twin screw extruder). The extruder consisted of 10 (electrically heated and water-cooled) barrels and a die head (21×Ø0.5 mm) with a screw diameter of 16 mm and a length to diameter ratio of 40. Demineralized water was injected into the second barrel. The temperature of barrels 1-3 was set to 80° C., and barrels 4-10 as well as the die head at 60° C. Molten Vitamin A acetate at 70° C. (optionally with added antioxidant such as d,l-alpha tocopherol or butylated hydroxytoluene (BHT)) was injected into barrel 5 and mixed with the modified food starch/dextrin in the downstream barrels. A typical extrudate strand composition is shown in Table 2. The extrudate strands containing the emulsified Vitamin A acetate droplets were directly cut at the die face by two rotating knives (Thermo Fisher Scientific). The cut, discrete solid particles were dried in a laboratory-scale fluid bed drier (Retsch TG 200) for 60 minutes at 50° C. to obtain a final water content of 6 wt %.

A few hundred milligrams of the discrete solid extruded particles were dissolved in water under gentle stirring and the Vitamin A acetate oil droplet size distribution was measured by laser diffraction with a Malvern Mastersizer 2000 and Hydro 2000 S sample dispersion unit. The resulting surface weighted mean oil droplet diameter ($d_{3,2}$) was 313 nm. The surface oil content of the particles (as determined by extraction with cyclohexane and defined as the content found by extraction over the total Vitamin A acetate content of the particle) was very low, 0.1%. The extruded particle size and shape analysis was performed with a Malvern Morphologi G3S microscope and corresponding software. A 1× objective was used. Perfectly spherical particles were defined with a HS Circularity ≥0.91 in the Morphologi G3S software and thereby a fraction of 8% spheres was found. The mean CE diameter of the thus determined particle number distribution was 695 µm.

TABLE 2

Extrudate strand composition as well as discrete solid extruded particle content of Example 2.

| Ingredient | Extrudate strand composition, wt % of total | Solid particle content, wt % of total |
|---|---|---|
| Modified food starch | 41 | 41.5 |
| Dextrin | 41 | 41.5 |
| Water | 7 | 6 |
| Vitamin A acetate | 11 | 11 |

Example 3

The production of discrete solid extruded particles comprising emulsified Vitamin A acetate was conducted according to the schematic process flow shown in FIG. 1. The emulsifiers (modified food starch) as well as the plasticizer (sorbitol) were both gravimetrically fed (Brabender Technologie) into the first barrel of a laboratory-scale co-rotating twin screw extruder (Thermo Fisher Scientific, HAAKE Polylab OS with PTW16/40 OS twin screw extruder). The extruder consisted of 10 (electrically heated and water-cooled) barrels and a die head (12×Ø0.5 mm) with a screw diameter of 16 mm and a length to diameter ratio of 40. Demineralized water was injected into the second barrel. The temperature of barrels 1-3 was set to 80° C., and barrels 4-10 as well as the die head at 60° C. Molten Vitamin A acetate at 70° C. (optionally with added antioxidant such as d,l-alpha tocopherol or butylated hydroxytoluene (BHT)) was injected into barrel 5 and mixed with the modified food starch/sorbitol in the downstream barrels. A typical extrudate strand composition is shown in Table 3. The extrudate strands containing the emulsified Vitamin A acetate droplets were collected and let to cool down to room temperature. Subsequently the strands were cut into discrete, solid particles with a pelletizer (Thermo Fisher Scientific) and finally dried in a laboratory-scale fluid bed drier (Retsch TG 200) for 60 minutes at 50° C. to obtain a final water content of 6 wt %.

A few hundred milligrams of the discrete solid extruded particles were dissolved in water under gentle stirring and the Vitamin A acetate oil droplet size distribution was measured by laser diffraction with a Malvern Mastersizer 2000 and Hydro 2000 S sample dispersion unit. The resulting surface weighted mean oil droplet diameter ($d_{3,2}$) was 144 nm. No surface oil was found at the particles (as determined by extraction with cyclohexane and defined as the content found by extraction over the total Vitamin A acetate content of the particle). The extruded particle size and shape analysis was performed with a Malvern Morphologi G3S microscope and corresponding software. A 1× objective was used. Perfectly spherical particles were defined with a HS Circularity ≤0.91 in the Morphologi G3S software and thereby a fraction of 20% spheres was found. The mean CE diameter of the thus determined particle number distribution was 498 µm.

TABLE 3

Extrudate strand composition as well as discrete solid extruded particle content of Example 3.

| Ingredient | Extrudate strand composition, wt % of total | Extruded solid particle content, wt % of total |
|---|---|---|
| Modified food starch | 62 | 65 |
| Sorbitol | 16 | 17 |
| Water | 10 | 6 |
| Vitamin A acetate | 12 | 12 |

The invention claimed is:

1. A process for production of substantially spherical discrete solid particles, wherein the process comprises:
   (i) emulsifying ingredients comprised of at least one fat-soluble compound and at least one emulsifier in an extruder to form oil-in-water emulsion droplets;
   (ii) extruding from the extruder substantially cylindrical extrudate strands comprising the oil-in-water emulsion droplets;
   (iii) forming discrete substantially cylindrical solid particles from the extrudate strands by cutting and drying; and thereafter
   (iv) subjecting the dried discrete substantially cylindrical solid particles to a spheronisation process to thereby form substantially spherical discrete solid particles therefrom.

2. The process according to claim 1, wherein the drying is practiced in any sequence of before, during and/or after cutting of the extrudate strands.

3. The process according to claim 1, wherein the fat-soluble compounds are oils or vitamins.

4. The process according to claim 1, wherein the fat-soluble compound is at least one selected from the group consisting of coconut oil, corn oil, cottonseed oil, olive oil, palm oil, peanut oil, rapeseed oil, canola oil, safflower oil, sesame oil, soybean oil, sunflower oil, hazelnut oil, almond oil, cashew oil, macadamia oil, mongongo nut oil, pracaxi oil, pecan oil, pine nut oil, pistachio oil, sacha Inchi (*Plukenetia volubilis*) oil, walnut oil, linoleic acid, arachidonic acid, γ-linolenic acid, dihomo-γ-linolenic acid, α-linolenic acid, eicosapentaenoic acid and docosahexaenoic acid, lipophilic plant extracts, vitamin A, vitamin A acetate, vitamin A palmitate, vitamin E, vitamin E acetate, vitamin K and vitamin D3.

5. The process according to claim 1, wherein the fat-soluble compound is at least one selected from the group consisting of corn oil, vitamin A, vitamin A acetate, vitamin A palmitate, vitamin E, vitamin E acetate, and polyunsaturated fatty acids.

6. The process according to claim 1, wherein the emulsifier is at least one selected from the group consisting of modified food starches, pectin, alginate, carrageenan, furcellaran, chitosan, maltodextrin, dextrin derivatives, cellulose acetate, methyl cellulose, hydroxypropyl methyl cellulose, gum acacia, gum arabic, flaxseed gum, ghatti gum, tamarind gum, arabinogalactan, bovine gelatine, fish gelatine, pork gelatine, poultry gelatin, plant proteins, lecithin, polyglycerol ester of fatty acids, monoglycerides of fatty acids, diglycerides of fatty acids, sorbitan ester, PG ester and sugar ester.

7. The process according to claim 1, wherein the oil-in-water emulsion comprises 5 wt.-% to 75 wt.-%, based on total weight of the oil-in-water emulsion, of the at least one fat-soluble compound.

8. The process according to claim 1, wherein the oil-in-water emulsion comprises 5 wt.-% to 80 wt.-%, based on total weight of the emulsion, of the at least one emulsifier.

9. The process according to claim 1, wherein the oil-in-water emulsion comprises 1 wt.-% to 90 wt.-%, based on total weight of the oil-in-water emulsion, of water.

10. The process according to claim 9, wherein the oil-in-water emulsion comprises 1 wt.-% to 80 wt.-%, based on the total weight of the emulsion, of water.

11. The process according to claim 1, wherein the oil-in-water emulsion comprises 1 wt.-% to 85 wt.-%, based on total weight of the emulsion, of at least one auxiliary agent.

12. The process according to claim 11, wherein the auxiliary agent is at least one selected from the group consisting of ascorbic acid or salts thereof, synthetic or natural tocopherol, butylated hydroxytoluene (BHT), butylated hydroxyanisole (BHA), ascorbyl palmitate, propyl gallate, tert. butyl hydroxyquinoline, ethoxyquin, ascorbic acid esters of fatty acids, fructose, glucose, glycerol, mannitol, invert sugar syrup, sorbitol, sucrose, xylitol, propylene glycol, esters of citric acid, lactitol, erythritol and maltitol, stabilisers, glycerine, sorbitol, polyethylene glycol, gellan gum, xanthan gum), dyes, fragrances, fillers and buffers.

13. The process according to claim 1, wherein the step (i) comprises sequentially adding the at least one emulsifier, water and the at least one fat-soluble compound to the extruder.

14. The process according to claim 13, wherein the at least one fat-soluble compound comprises vitamin A or an ester derivative thereof.

15. The process according to claim 1, wherein the at least one fat-soluble compound comprises vitamin A or an ester derivative thereof and wherein the process comprises adding the vitamin A or ester derivative thereof to the extruder in liquid form at a beginning stage of the process.

16. The process according to claim 1, wherein the at least one fat-soluble compound comprises vitamin A or an ester derivative thereof and wherein process comprises adding the vitamin A or ester derivative thereof as a pure powder or in a mixture with at least one modified food starch either at a beginning stage of the process or at any stage thereafter.

17. The process according to claim 1, wherein the extruder is operated at an inside temperature of between 20° C. and 220° C.

18. The process according to claim 1, wherein the total residence time in the extruder for the ingredients is between 1 and 400 s.

19. Substantially spherical discrete solid extruded particles comprising oil-in-water emulsion droplets, wherein the oil-in-water emulsion droplets are comprised of:
   at least one fat soluble compound,
   at least one emulsifier,
   water, and optionally
   at least one auxiliary agent, wherein
   the oil-in-water emulsion droplets have an average particle size of less than 300 nm, and wherein
   the discrete solid extruded particles have a water content which is less than 10 wt-%, based on total weight of the discrete solid extruded particles, and wherein
   the substantially spherical discrete solid extruded particles have a High Sensitivity (HS) circularity of ≥0.91.

20. The particles according to claim 19, wherein the particles have a size of less than 1000 μm.

21. The particles according to claim 19 comprising:
   5 wt.-% to 75 wt.-%, based on total weight of the discrete solid extruded particles, of the at least one fat-soluble compound, 5 wt.-% to 80 wt.-%, based on the total weight of the discrete solid extruded particles, of the at least one emulsifier, less than 10 wt.-%, based on the total weight of the discrete solid extruded particles, of water, and optionally 1 wt.-% to 85 wt.-%, based on the total weight of the discrete solid extruded particles, of the at least one auxiliary agent.

22. The particles according to claim 19, comprising 8 wt.-% to 70 wt.-%, based on total weight of the discrete solid extruded particles, of the at least one fat-soluble compound, wherein the at least one fat-soluble compound is selected from the group consisting of coconut oil, corn oil, cottonseed oil, olive oil, palm oil, peanut oil, rapeseed oil, canola oil, safflower oil, sesame oil, soybean oil, sunflower oil, hazelnut oil, almond oil, cashew oil, macadamia oil, mongongo nut oil, pracaxi oil, pecan oil, pine nut oil, pistachio oil, sacha Inchi (*Plukenetia volubilis*) oil, polyunsaturated fatty acids (PUFAs), nutraceuticals, vitamin A, vitamin A acetate, vitamin A palmitate, vitamin E, vitamin E acetate, vitamin K and vitamin D3.

23. The particles according to claim 19, comprising 8 wt.-% to 80 wt.-%, based on total weight of the discrete solid extruded particles, of the at least one emulsifier, wherein the at least one emulsifier is selected from the group consisting of modified (food) starches, pectin, alginate, carrageenan, furcellaran, chitosan, maltodextrin, dextrin derivatives, cellulose acetate, methyl cellulose, hydroxypropyl methyl cellulose, lignosulfonate, gum acacia, gum arabic, flaxseed gum, ghatti gum, tamarind gum, arabinogalactan), bovine gelatine, fish gelatine, pork gelatine, poultry) gelatine, plant proteins, animal proteins, lecithin, polyglycerol esters of fatty acids, monoglycerides of fatty acids, diglycerides of fatty acids, sorbitan ester, PG esters and sugar esters.

24. The particles according to claim 19, wherein the particles comprise water in an amount less than 6 wt.-%, based on total weight of the discrete solid extruded particles, of water.

25. The particles according to claim 19, wherein the particles comprise the at least one auxiliary agent in an amount of 1 wt.-% to 80 wt.-%, based on total weight of the discrete solid extruded particles, and wherein the at least one auxiliary agent is selected from the group consisting of ascorbic acid or salts thereof, synthetic or natural tocopherol, butylated hydroxytoluene (BHT), butylated hydroxyanisole (BHA), ascorbyl palmitate, propyl gallate, tert. butyl hydroxyquinoline, ethoxyquin, ascorbic acid esters of fatty acids, fructose, glucose, glycerol, mannitol, invert sugar syrup, sorbitol, sucrose, xylitol, propylene glycol, esters of citric acid, lactitol, erythritol and maltitol, stabilisers, glycerine, sorbitol, polyethylene glycol, gellan gum, xanthan gum), dyes, fragrances, fillers and buffers.

26. A food, feed, pharmaceutical or personal care product comprising particles according to claim 19.

* * * * *